United States Patent [19]

Stern et al.

[11] Patent Number: 5,443,470

[45] Date of Patent: * Aug. 22, 1995

[54] METHOD AND APPARATUS FOR ENDOMETRIAL ABLATION

[75] Inventors: Roger A. Stern, Cupertino; Vincent N. Sullivan; Robert L. Marion, both of San Jose, all of Calif.

[73] Assignee: Vesta Medical, Inc., Palo Alto, Calif.

[*] Notice: The portion of the term of this patent subsequent to Jan. 11, 2011 has been disclaimed.

[21] Appl. No.: 46,683

[22] Filed: Apr. 14, 1993

Related U.S. Application Data

[63] Continuation-in-part of Ser. No. 877,567, May 1, 1992, Pat. No. 5,277,201.

[51] Int. Cl.$^6$ .............................................. A61N 5/00
[52] U.S. Cl. ..................................... 607/98; 607/99; 607/113; 607/138; 606/32; 606/41
[58] Field of Search ........................ 606/27, 28, 32, 33, 606/40, 41, 45, 49; 607/98, 99, 113, 116, 138, 148

[56] References Cited

U.S. PATENT DOCUMENTS

| | | |
|---|---|---|
| 1,827,306 | 10/1931 | Chapman et al. . |
| 3,324,847 | 6/1967 | Zoumboulis . |
| 3,369,549 | 2/1968 | Armao . |
| 3,750,653 | 8/1973 | Simon . |
| 3,789,829 | 2/1974 | Hassen . |
| 3,840,016 | 10/1974 | Lindemann . |
| 3,901,224 | 8/1975 | Bucalo . |
| 3,924,628 | 12/1975 | Droegemueller et al. . |
| 3,934,580 | 1/1976 | Cournut . |
| 4,014,988 | 3/1977 | Pharriss et al. . |
| 4,016,270 | 4/1977 | Pharriss et al. . |

(List continued on next page.)

FOREIGN PATENT DOCUMENTS

| | | | |
|---|---|---|---|
| 0115420 | 8/1984 | European Pat. Off. . | |
| 0407057 | 1/1991 | European Pat. Off. . | |
| 8527331.7 | 9/1985 | Germany . | |
| 3516830 | 11/1986 | Germany | 607/116 |
| WO87/01276 | 3/1987 | WIPO . | |

OTHER PUBLICATIONS

"Hyperthermia Overview Using Microwave Antennas", Invited Lectures, Thomas P. Ryan, M.D. Thermoradiotherapy, C. T. Coughlin, M.D.

"Devices: Replacing the Roto-Rooter", Trends, Michael Dolan.

(List continued on next page.)

Primary Examiner—Lee S. Cohen
Attorney, Agent, or Firm—Oblon, Spivak, McClelland, Maier & Neustadt

[57] ABSTRACT

An endometrial ablation apparatus and method wherein an RF current having a frequency of between 250 kHz and 100 MHz is passed through the entire surface of an endometrium in order to provide heating of the endometrium. An electroconductive expandable member such as a balloon is used as the medium for passing the current and causing the heating of the endometrium. The temperature of the endometrium is raised to a temperature between 45° C. and 90° C. and preferably not above 70° for a time sufficient to destroy the cells of the lining while maintaining the average temperature of the myometrium at a temperature below approximately 42° C. The expandable balloon is connected to a power source which provides the radio frequency power having the desired characteristics to selectively heat the endometrial lining to the desired temperature. The balloon can be constructed with an electroconductive elastomer such as a mixture of polymeric elastomer and electroconductive particles or can be a non-extensible bladder having a shape and a size, in its fully expanded form, which will extend the organ and effect contact with the endometrial lining to be destroyed. The electroconductive member may consist of a plurality of electrode area segments having a thermistor associated with each electrode segment whereby the temperature from each of said plurality of segments is monitored and controlled by a feedback arrangement from the thermistors.

22 Claims, 13 Drawing Sheets

U.S. PATENT DOCUMENTS

| | | |
|---|---|---|
| 4,072,147 | 2/1978 | Hett . |
| 4,102,342 | 7/1978 | Akiyama et al. . |
| 4,160,455 | 7/1979 | Law . |
| 4,198,981 | 4/1980 | Sinnreich . |
| 4,292,960 | 10/1981 | Paglione . |
| 4,296,760 | 10/1981 | Carlsson et al. . |
| 4,311,154 | 1/1982 | Sterzer et al. . |
| 4,349,033 | 9/1982 | Eden . |
| 4,375,220 | 3/1983 | Matvias . |
| 4,377,168 | 3/1983 | Rzasa et al. . |
| 4,409,993 | 10/1983 | Furihata . |
| 4,469,103 | 9/1984 | Barrett . |
| 4,491,131 | 1/1985 | Vassiliadis . |
| 4,494,539 | 1/1985 | Zenitani et al. . |
| 4,549,533 | 10/1985 | Cain et al. . |
| 4,552,127 | 11/1985 | Schiff . |
| 4,572,190 | 2/1986 | Azam et al. . |
| 4,622,972 | 11/1986 | Giebeler, Jr. . |
| 4,638,436 | 1/1987 | Badger et al. . |
| 4,658,836 | 4/1987 | Turner . |
| 4,662,383 | 5/1987 | Sogawa et al. . |
| 4,674,481 | 6/1987 | Boddie, Jr. et al. . |
| 4,676,258 | 6/1987 | Inokuchi et al. . |
| 4,692,452 | 9/1987 | Cerny et al. . |
| 4,700,701 | 10/1987 | Montaldi . |
| 4,754,752 | 7/1988 | Ginsburg et al. . |
| 4,754,757 | 7/1988 | Feucht . |
| 4,758,592 | 7/1988 | Horrobin et al. . |
| 4,771,778 | 9/1988 | Mar . |
| 4,773,899 | 9/1988 | Spears . |
| 4,776,349 | 11/1988 | Nashef et al. . |
| 4,818,954 | 4/1989 | Flachenecker et al. . |
| 4,823,812 | 4/1989 | Eshel et al. . |
| 4,836,189 | 6/1989 | Allred, III et al. . |
| 4,852,579 | 8/1989 | Gilstad et al. . |
| 4,860,752 | 8/1989 | Turner . |
| 4,865,047 | 9/1989 | Chou et al. . |
| 4,927,413 | 5/1990 | Hess . |
| 4,935,003 | 6/1990 | Gainutdinova et al. . |
| 4,938,217 | 7/1990 | Lele . |
| 4,946,440 | 8/1990 | Hall . |
| 4,949,718 | 8/1990 | Newwirth et al. . |
| 4,955,377 | 9/1990 | Lennox et al. . |
| 4,960,109 | 10/1990 | Lele . |
| 4,961,435 | 10/1990 | Kitagawa et al. . |
| 4,967,765 | 11/1990 | Turner et al. . |
| 4,974,587 | 12/1990 | Turner et al. . |
| 4,979,948 | 12/1990 | Geddes et al. . |
| 4,985,027 | 1/1991 | Dressel . |
| 4,993,430 | 2/1991 | Shimoyama et al. . |
| 4,997,653 | 3/1991 | Igarashi . |
| 4,998,930 | 3/1991 | Lundahl . |
| 5,003,991 | 4/1991 | Takayama et al. . |
| 5,006,119 | 4/1991 | Acker et al. . |
| 5,026,959 | 6/1991 | Ito et al. . |
| 5,032,124 | 7/1991 | Menton . |
| 5,035,694 | 7/1991 | Kazprzyk et al. . |
| 5,041,089 | 8/1991 | Mueller et al. . |
| 5,045,056 | 9/1991 | Behl . |
| 5,050,597 | 9/1991 | Daikuzono . |
| 5,057,106 | 10/1991 | Kasevich et al. ............... 606/33 |
| 5,059,191 | 10/1991 | Beyer et al. . |
| 5,084,044 | 1/1992 | Qunit . |
| 5,092,841 | 3/1992 | Spears . |
| 5,098,429 | 3/1992 | Sterzer . |
| 5,100,388 | 3/1992 | Behl et al. . |
| 5,188,122 | 2/1993 | Phipps et al. ............... 607/138 |
| 5,248,312 | 9/1993 | Langberg ............... 607/113 |
| 5,277,201 | 1/1994 | Stern ............... 607/98 |

OTHER PUBLICATIONS

"Endometrial Ablation", Therapeutic Hysteroscopy: Indications and Techniques, pp. 148-163, W. W. Babcock et al.

"Uterine Resectoscopes for Endometrial Ablation and Resection", Karl Storz.

"Treatment of Menorrhagia by Radiofrequency Heating", Int. J. Hyperthermai, 1991, vol. 7, No. 2, 213-220, M. V. Prior et al.

"Treatment of Functional Menorrhagia by Radiofrequency-Induced Thermal Endometrial Ablation", The Lancet, Feb. 17, 1990, pp. 374-376, J. H. Phipps et al.

"Resectoscopes for the Gynecologist", Contemporary OB/GYN, Philip G. Brooks, M.D., pp. 51-57.

"New Techniques in Operative Hysteroscopy", Audio-Digest Obstetrict/Gynecology, vol. 37, No. 10, May 15, 1990, Bruce McLucas et al.

"New Concepts in Hysteroscopy", Symposium, Contemporary OB/GYN, pp. 84-103, Michael S. Baggish, M.D. et al.

"Microwave Applicator for Transurethral Hyperthermia of Benign Prostatic Hyperplasia", Int. J. Hyperthermia, 1989, vol. 5, No. 3, 283-296, M. A. Astrahan et al.

"Endometria Ablatin: An Alterative to Hysterectomy", The American Journal of Gynecologic Health, vol. V, No. 3, Thierry G. Vancaillie, M.D.

"A Technique for Combining Microwave Hyperthermia with Intraluminal Brachytherapy of the Oesophagus", Int. J. Hyperthermia, 1989, vol. 5, No. 1, 37-51, N. A. Astrahan et al.

METHOD AND APPARATUS FOR ENDOMETRIAL ABLATION

CROSS-REFERENCE TO RELATED APPLICATION

This is a continuation-in-part of application Ser. No. 07/877,567 filed May 1, 1992, now U.S. Pat. No. 5,277,201.

BACKGROUND OF THE INVENTION

1. Field of the Invention

The present invention relates to a method and an apparatus for in situ destruction of the inner lining of body organs, and more particularly the providing of a selective destruction of the endometrium as an alternative to hysterectomy for treatment of uterine bleeding.

2. Discussion of Background

Prior techniques for removing or destroying the inner lining of body organs have been explored in order to provide for an alternative to surgical removal of the body organs for treatment of diseases and other abnormal conditions. Prior techniques involved the destructive treatment of the inner linings with chemicals and with various forms of thermal energy such as radio frequency, microwave heating, cryotherapy, laser surgery and electrosurgery. Radio frequency and microwave energies have also been applied directly to the linings to generate heat in situ.

One type of thermal destruction is described in U.S. Pat. No. 4,979,949 wherein thermal ablation of the mucosal layer of a gall bladder is accomplished by resistive heating with an RF balloon electrode. Electric current is delivered from the balloon by a conductive expansion liquid filling the balloon. This device has power loss which occurs in the conductive fluid and it cannot be adapted for anything but a single electrode arrangement and it lacks a complete individual power control and/or temperature sensor.

In another example of prior art treatment, balloon catheters have been supplied with a heated fluid for thermal ablation of hollow body organs as described in U.S. Pat. No. 5,045,056. Furthermore, application of microwave and high frequency RF energy to body areas to destroy body tissue, using single electrodes enclosed in expanded balloons have been described in U.S. Pat. No. 4,662,383 and U.S. Pat. No. 4,676,258.

The disadvantage of the procedures occurring in the prior art such as described above include a lack of uniform large area treatment because these procedures involve a lack of uniform control or temperature sensing ability to ensure complete ablation.

Other procedures developed to date involve manual applications of small treatment tools to successive areas of the lining which is an expensive operating room procedure and which, similar to the other previous heat balloon treatments, involve limited assurance of uniform results.

SUMMARY OF THE INVENTION

Accordingly, one object of the present invention is to provide a novel method and apparatus for performing safe and rapid endometrial ablation without the need for visual contact during the ablation of the lining.

It is a further object to provide an apparatus and a method for endometrial ablation which can be carried out on an out-patient basis without requiring the use of an operating room.

The objects of the invention are carried out by a method which utilizes an electrically conductive or conductively coated expandable member conforming to the inner surface of the endometrium. The expandable member is filled with an electrically non-conductive medium and a RF current is passed through substantially the entire surface of the endometrium. The current is sufficient to resistively heat the endometrium in a single Operation to a temperature within a range of between 45° C. to 90° C. for a time sufficient to destroy the cells of the lining while maintaining the average temperature of the myometrium at a temperature of substantially 42° C. or less. The RF current has a frequency of at least 250 kHz and less than 100 MHz.

The method according to the present invention involves the insertion of a conductive, expandable member in its unexpanded state into the uterine cavity through the cervical opening and subsequently expanding the member to establish surface contact with the endometrial surface and applying the RF current to the member in its expanded condition.

It is a further object of the present invention to provide that the electroconductive expandable member includes a thin bladder having an array of separate electrodes on one surface and further having a temperature sensor associated with each separate electrode in order to provide a feedback temperature sensor for each electrode. The plurality of separate electrodes are independently and sequentially energized with thermistor temperature feedback to bring the endometrial temperature to a desired level.

It is further an object of the present invention to provide electrodes having a specific configuration so that the heating is not concentrated at the edges of the electrode and so that uniform heating is achieved over the entire electrode surface by providing a plurality of throughholes throughout the electrode or by forming the electrode in a pattern of lines, thereby creating a uniform density of edges and equalizing the current density across the surface area of the electrode.

It is a further object of the present invention to provide an electronic control means capable of controlling the output of a conventional electrosurgical power source and delivering power from the power source sequentially, and in a controlled manner, to the electrodes of the balloon.

It is a further object of the present invention to provide a disposable handheld applicator and electrode assembly combination to deliver the ablation device to the uterus and to retract the device upon completion of the ablation.

It is a further object of the present invention to provide an array of separate electrodes and associated separate thermistors on an expandable member with a series of power leads with each power lead delivering power to a single electrode and to its associated thermistor to provide a temperature feedback for temperature regulation of the endometrial ablation.

It is a further object of the present invention to provide an inner lumen having the ability to contain a fiber optic image conduit which serves as a visual aid when placing the device.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
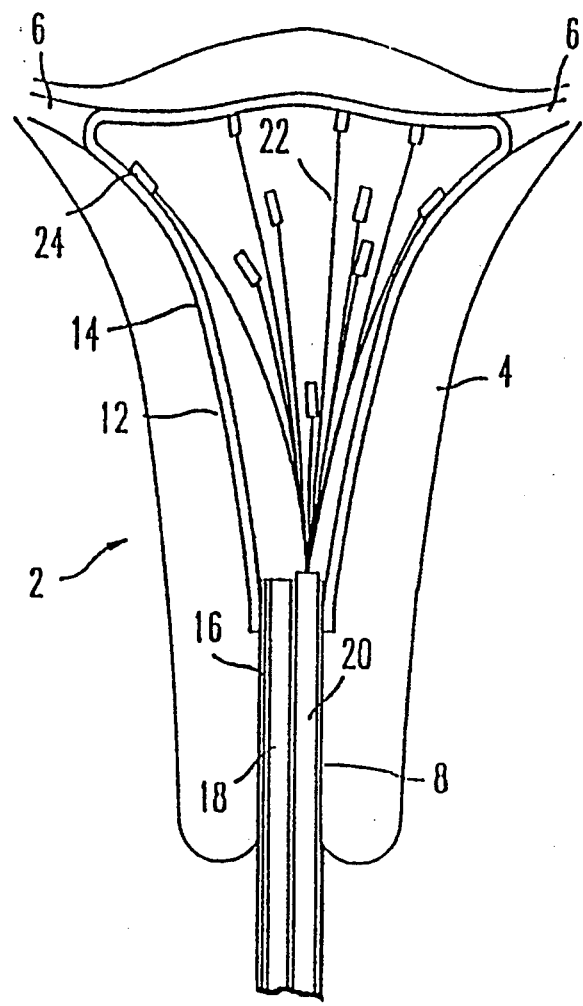
FIG. 1 is a cross-sectional representation of an electroconductive balloon as an expandable member in an expanded format in place in a uterus.
Figure 2:
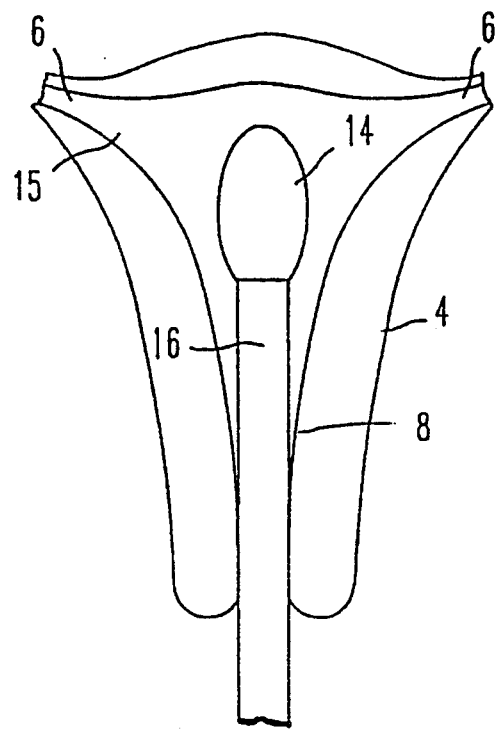
FIG. 2 is a representation of the apparatus of FIG. 1 in an unexpanded condition.

Referring now to the drawings, wherein like reference numerals designate identical or corresponding parts throughout the several views, and more particularly to FIG. 1 thereof, a cross-sectional representation of the invention utilizes an electroconductive balloon as the expandable member with FIG. 2 representing the same apparatus as FIG. 1 prior to inflation of the balloon element. The uterus 2 consists of myometrial tissue 4 surrounding the uterine cavity. The normal uterine cavity or envelope is a flat cavity having approximately the shape of an inverted triangle with the two upper corners communicating with the ovaries by way of the fallopian tubes 6 in the bottom corner opening into the cervical canal 8. The entire surface of the envelope includes the entrance of the fallopian tubes 6 and the cervical canal 8 which is covered with a thin layer of tissue known as uterine endometrium. The selective destruction of the endometrial cells is the goal of the improved method and apparatus disclosed in this present invention.

The monopolar electrode system developed in conjunction with FIG. 1 expands to conform to the endometrial surface to be treated and this in turn dilates and stretches the endometrium to reduce surface folds. Radio frequency electric current passes through the dilated endometrial surface for a time sufficient to destroy the endometrial cells by elevating the temperature of the endometrium to between 45° C. and 90° C., and preferably within 10 seconds. The temperature is maintained until the endometrial tissue is destroyed which is optimally accomplished by a temperature between 55° C. to 65° C. for up to 10 minutes.

The electric current passes through or along the surface of the expandable member and the interior of the expandable member is filled with an electrically non-conductive substance such as a fluid or gas. The expandable member can be any material or article which can be compressed or otherwise prepared in a small diameter configuration for insertion through the cervix and expanded or inflated after insertion to provide the dilation. This expandable member establishes direct electrical connection or capacitive coupling with the endometrium. A second electrical contact can occur by way of grounding plates or patches which contact a large area of the patient's skin in order to complete the electrical circuit.

Electric current flowing through the tissue causes resistive heating. The power density diminishes with distance from the electrode as the reciprocal of the fourth power of the distance. Thus, any heat generated is focused in the endometrium and the immediately surrounding muscular tissue which in the particular case of the present invention is the portion of the myometrium in contact with the lining. Because the myometrium 4 is highly vascularized, heat removal occurs rapidly. As a result, the temperature of the endometrium 12 can be heated to a destructive temperature faster than the myometrium 4 and the rest of the uterus. Therefore, because of this temperature relationship, endometrial ablation can be safely accomplished as a simple medical procedure using local anesthesia. Furthermore, it can be a service made available at a fraction of the cost of prior art systems with less hazard than other endometrial ablations.

The inflatable balloon or bladder 14 is inserted into the uterine cavity 15 as shown in FIG. 2 and subsequently the inflation of the balloon occurs with a gas or a non-conductive liquid so that it extends and fills the uterine cavity conforming to the expanded surface as shown in FIG. 1. Portions of the balloon 14 extend into the entrance to the fallopian tubes 6 and extend along the entire endometrial surface 12 to the cervix 8. The balloon is attached to and forms a fluid-tight seal with the tube 16 which encloses a smaller fluid delivery tube 18 as well as an electrical cable 20 containing leads for the conductor as well as additional leads for the sensors. A plurality of temperature sensors 24 are shown attached to the inner surface of the balloon. Alternatively, this lead configuration can be replaced by lead pairs 22 for each sensor. The temperature sensors 24 are conventional thermistors or thermocouples and are positioned on zones of the balloon which will contact areas of the endometrial surface which are most sensitive to overheating. The temperature sensors can also be fiber optic temperature sensors. The fluid delivery tube 18 is connected to a source of gas or liquid through a conventional fluid control system which will be later illustrated in conjunction with FIG. 13.

Figure 3:
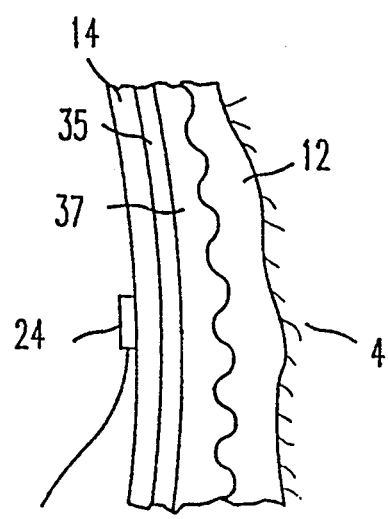
FIG. 3 is an enlarged cross-section illustrating the relationship between a small segment of the uterine endometrium and the expanded member.

The FIG. 3 is an enlarged cross-section illustrating the relationship between a small segment of uterine endometrium and the expandable balloon element of the FIG. 1. The endometrial lining 12, supported on the myometrium 4, is typically an irregular surface even after it is extended by the inflated balloon 14. Electrical contact between the conductive surface 35 on the outer surface of the balloon 14 and the endometrium 12 can be improved by covering the outer surface of the balloon 14 with a conventional electroconductive solution, paste or gel 37 which is physiologically non-toxic and non-irritating. Suitable electroconductive media including the known types of gels and pastes used as surface coatings for defibrillators may be used. Examples of suitable conductive gels are carboxymethylcellulose gels made from aqueous electrolyte solutions such as physiological saline solutions and the like. The electroconductive solution, paste or gel enhances electrical contact between the balloon and the endometrium by filling the pores of the balloon surface and the irregularities in the endometrial surface.

The expandable balloon or bladder can be an elastomeric polymer such as a natural or synthetic rubber made conductive by mixing the polymer with electroconductive particles such as carbon or conductive metal particles. Alternately, it may be made conductive by a surface coating of electroconductive material such as an electroconductive gel, or a conductive metal coating on the outer or inner surface of the balloon or bladder wall. Electroconductive coating can be applied to organic polymer surfaces by conventional vapor deposition, electrical depositions, sputtering and the like.

A preferred balloon comprises a thin, non-extensible polymer film such as a polyester or other flexible thermoplastic or thermosetting polymer film, for example, having a conductive metal coating on the outer or inner surface thereof. The films form a non-extensible bladder having a shape and size, in its fully expanded form, which will extend the organ and effect contact with the endometrial lining to be destroyed. The inner surface of the non-extensible bladder can be coated with electroconductive material which will capacitively couple to the endometrium provided that the bladder wall thickness is less than approximately 0.25 mm.

The surface of the expandable member can be an open-cell, porous material such as a foam or similar caged network of material which can hold a quantity of the electroconductive solution, paste or gel required to secure satisfactory electrical contact with the opposed endometrial surface. The surface can be coated with or impregnated with the electroconductive substance.

Figure 4B:
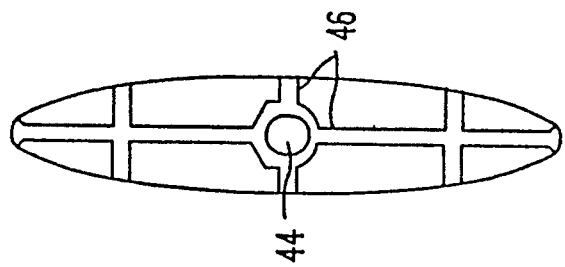
FIGS. 4a-b is a representation of an embodiment of an expandable member which uses a plurality of surface segments with each surface segment having a separate conductive surface and a temperature sensor.
Figure 4A:
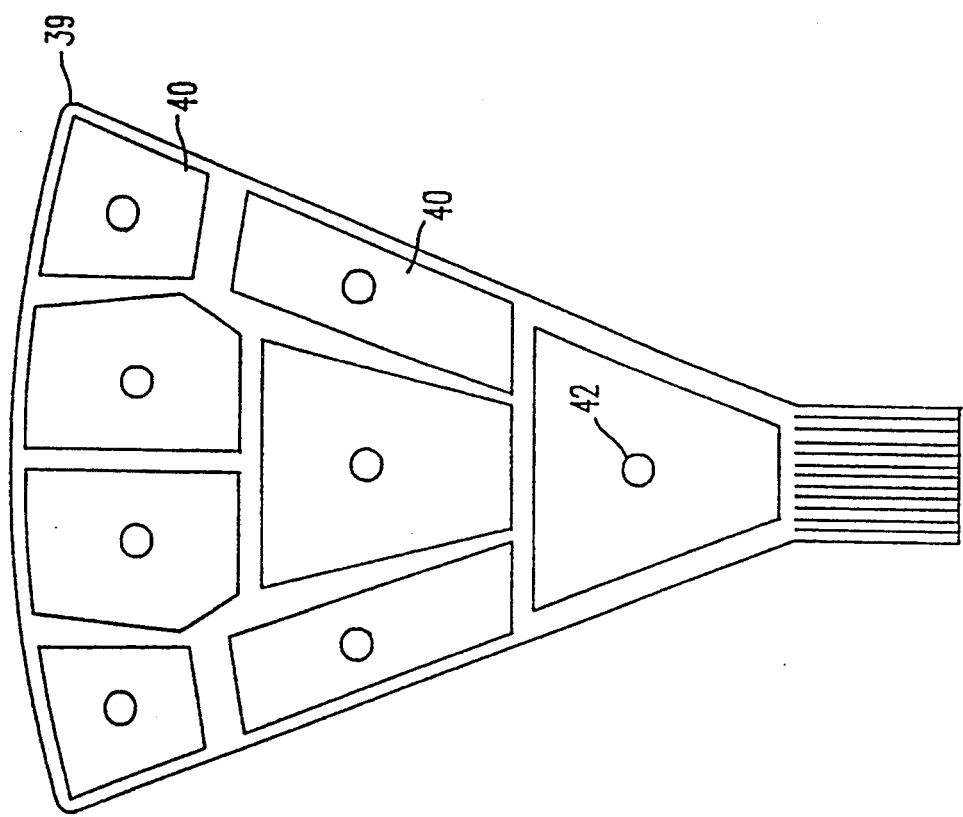

FIG. 4 illustrates an embodiment using a balloon with a plurality of surface segments as the expandable bladder 39. Each of the surface segments has a conductive surface and a temperature sensor. In this particular embodiment, the balloon has a segmented electrode coating of electroconductive metal on either the inner or the outer surface to permit controlled delivery of power to each segment. Each segment 40 is electrically connected through conventional leads to a power source (not shown in FIG. 4). Each conductive segment 40 also has a thermistor 42 which is connected through conventional leads to a switch matrix. FIG. 4B illustrates a top view of the bladder 39 and particularly features a lumen 44 extending through the center of the bladder 39. The lumen allows for light guides to be inserted through the center of the electrode. In other words, there is an inner lumen tube 44 attached to the center of the flat film.

Figure 5A:
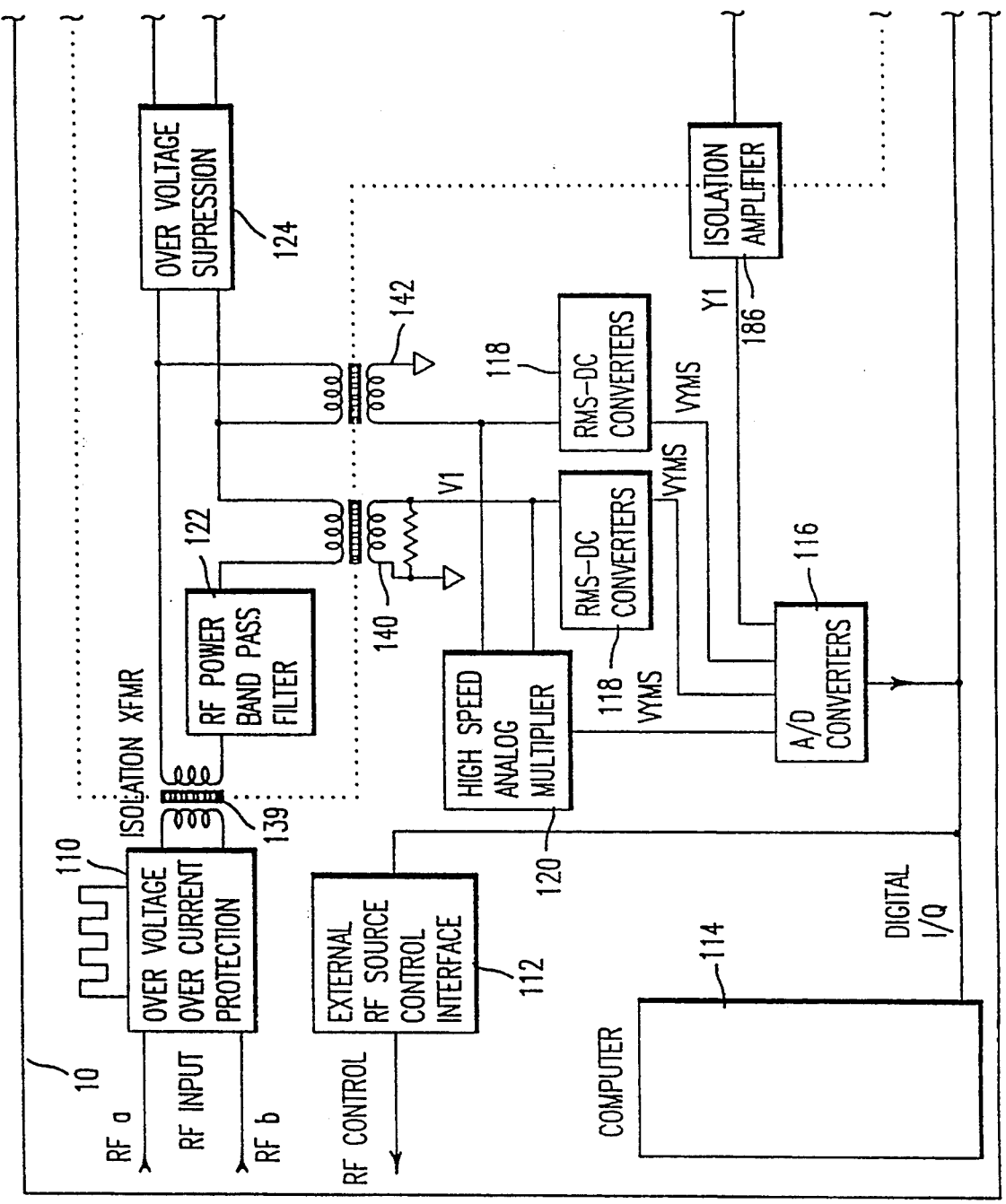
FIGS. 5a-b is a schematic representation of the power control system for the multi-segment element shown in FIG. 4.
Figure 5B:
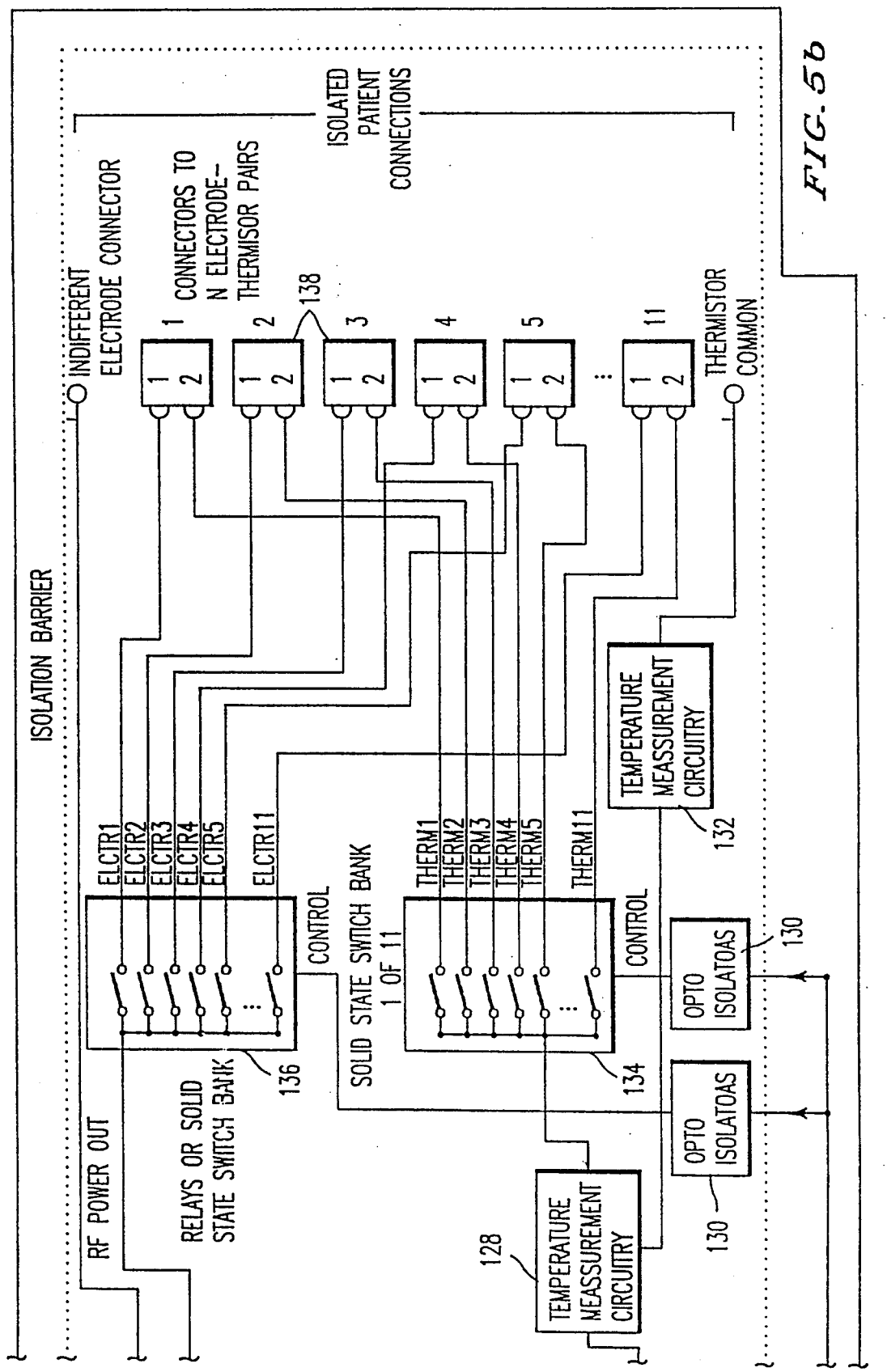

FIG. 5 is a schematic representation of the power source controller and the switch matrix for the multi-segment balloon discussed above in conjunction with, for example, FIG. 4. The electrical leads connect to the electro-thermistor pairs of the bladder of FIG. 4 by way of connectors 138 as shown in FIG. 5. The thermistor leads are connected to the matrix switch bank 134 and the electrode leads are connected to the switch bank 136. Each thermistor (FIG. 4a) 42 is sampled by means of the temperature measurement circuitry 128 and the isolation amplifier 126 before being converted in the converter 116 and fed to the computer 114. The temperature measurement circuitry compares the measured temperature with a thermistor reference voltage 132. The electrode switch 136 is controlled in response to the output of the computer 114 by means of the opto-isolators 130. Input power from the RF input passes through the overvoltage and overcurrent protector 110 and is filtered by the bandpass filter 122 before being subjected to overvoltage suppression by the suppression unit 124. The voltage is isolated by means of the transformers 139, 140 and 142 with the transformer voltages $V_i$ and $V_v$ from the transformers 140 and 142 being converted by the RMS-DC converters 118 into an RMS voltage to be fed to the converters 116. Prior to conversion, the signals $V_i$ and $V_v$ are also fed to a high-speed analog multiplier 120 RF control from computer 114 is provided through interface 112.

Figure 6:
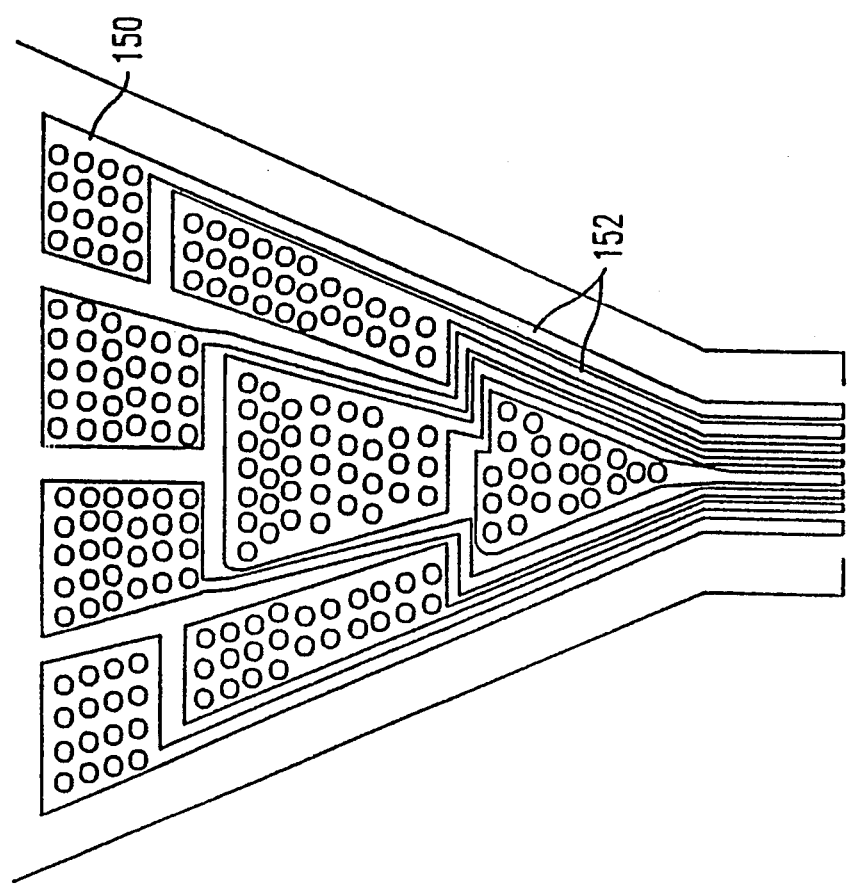
FIG. 6 illustrates an embodiment of the multi-segment element having perforated electrodes with illustrated power traces on the outside surface of the expandable member.

A variation of the electrode structure of FIG. 4 is shown in FIG. 6 wherein there are perforated electrodes 150 illustrated with their power traces 152. This particular electrode bladder of FIG. 6 is shown with the perforated electrode 150 on the exterior of the bladder.

Figure 7:
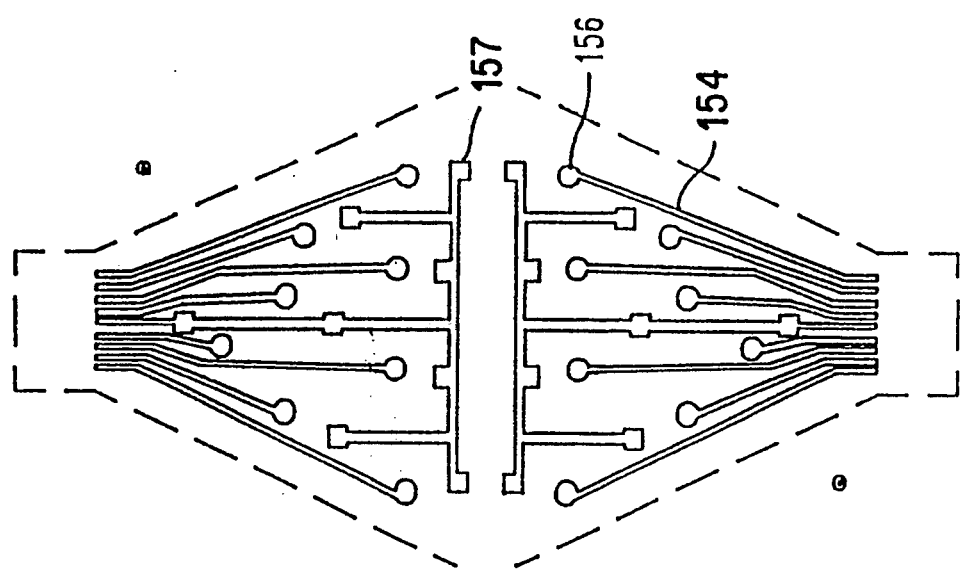
FIG. 7 illustrates thermistor traces and circular wiring jumper mounting pads on the interior of the expandable member.

FIG. 7 illustrates thermistor common-side traces 154 on the interior of the bladder with circular wiring jumping pads 156 with mounting sites 157 serving as the base for the thermistors. The common-side traces provide power for both the electrodes and the associated thermistor. The FIG. 7 illustrates both interior sides of the bladder.

Figure 8A:
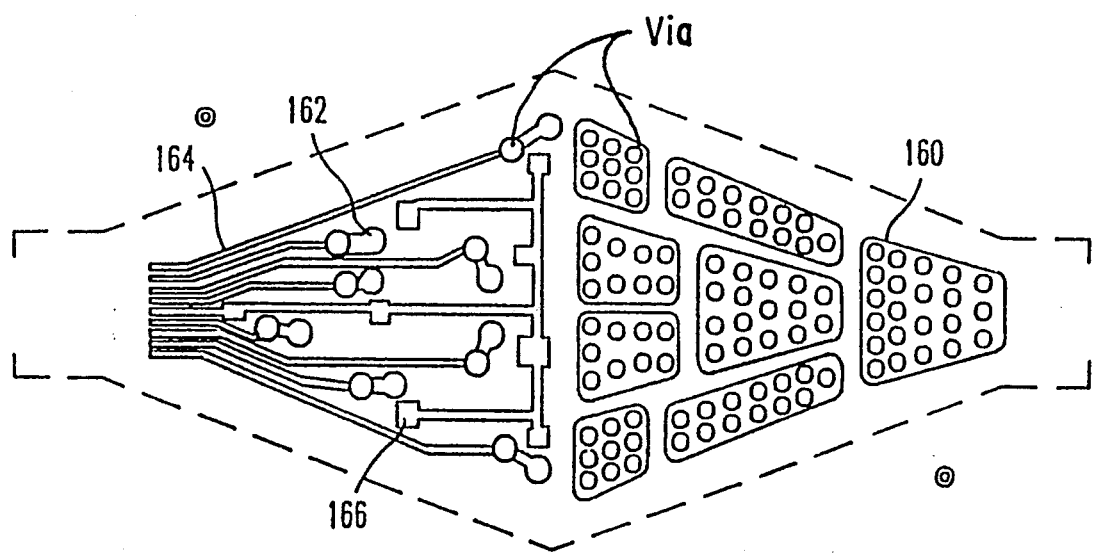
FIGS. 8a and 8b illustrates the double-sided electrode/thermistor traces on the respective inside and outside portions of the expandable member of FIGS. 6 and 7.
Figure 8B:
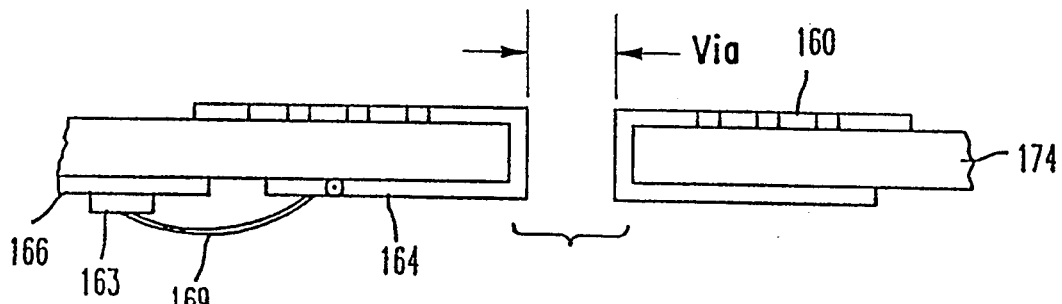

FIGS. 8a–b illustrates both the outside and the inside of a double-sided electrode with thermistor traces having perforated electrodes 160 on the outside and thermistor wiring pads 162 and electrode power leads 164 as well as thermistor mounting sites 166 on the inside. The connection between the inside and outside of the bladder is shown by the continuity labeled Via in the FIGS. 8a and 8b. FIG. 8b specifically shows a cross-sectional view of the bladder with the electrode 160 on the top or outside surface and the power traces 164 and thermistor wiring pad and mounting site 166 on the lower or inside surface. FIG. 8b illustrates the mounting of the thermistor 163 on the mounting site 166 with a connection between the power trace 164 and the thermistor 163 being made by the thermistor lead 169. FIG. 8b clearly illustrates that all except one of the holes in the perforated electrode 160 have a depth which reaches to the substrate or bladder 174. The one hole labelled Via extends through the entirety of the bladder as an electrical connection between the perforated electrode 160 and the power trace 164 on the bottom or inside surface. The FIG. 8a embodiments corresponds to a combination of the inside illustration of the power traces and the bonding surfaces from FIG. 7 along with the perforated electrode of FIG. 6 with the exception that FIG. 8a has the power traces on the inside surface whereas the embodiment of FIG. 6 has the power traces for the perforated electrodes on the outside surface.

Each of the views of FIGS. 6, 7 and 8, whether on the inside or the outside must be understood to represent only two surfaces of a bladder which must necessarily have four surfaces. The bladder, prior to inflation, can be envisioned as triangular with two outside triangular surfaces (top and bottom) and two inside triangular surfaces prior to inflation.

Figure 9:
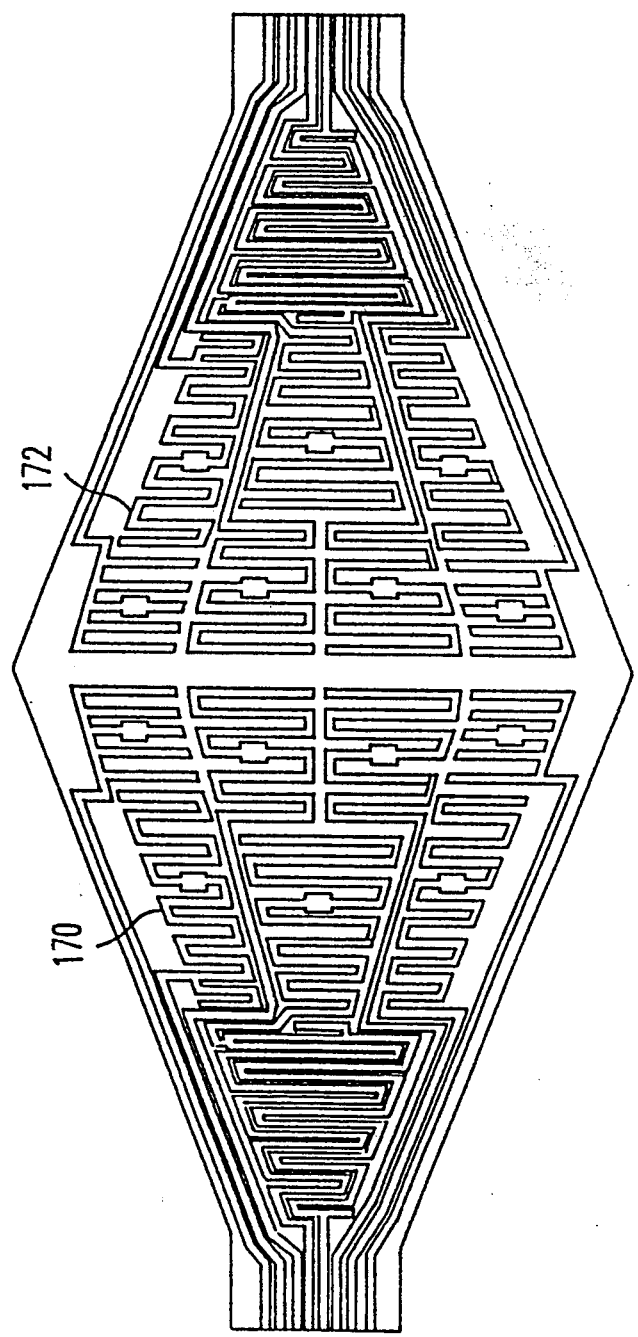
FIG. 9 illustrates an embodiment utilizing flat metallized stock material to be adhesively bonded to the expandable member with the material being arranged in a serpentine configuration.

A further variation of the electrode structure is shown in FIG. 9 which illustrates a flat metallized stock material adhesively bonded as electrodes 170 and 172 to the outside of both the top and the bottom of the bladder. The electrodes, which are metallized and adhesively bonded, form a serpentine electrode pattern in order to promote uniform heating of the area.

Figure 10A:
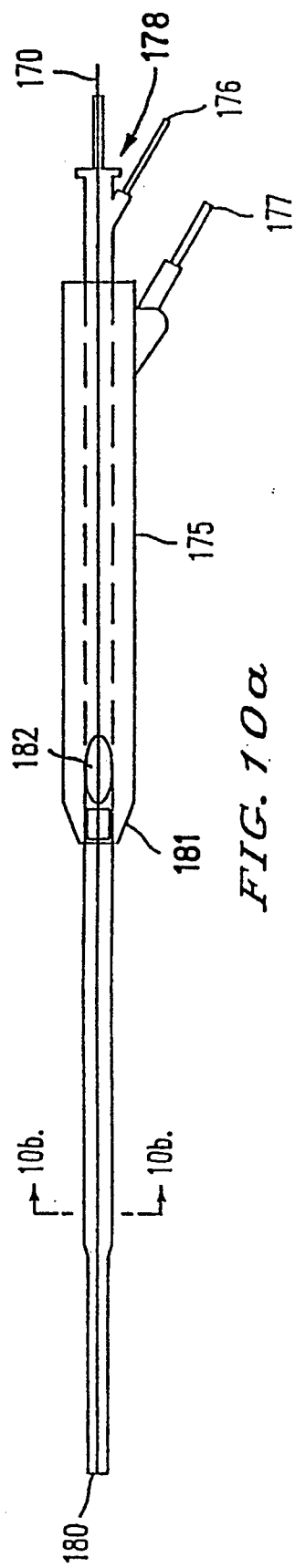
FIGS. 10a-b show the bladder device for delivering the expandable member to the uterus.
Figure 10B:
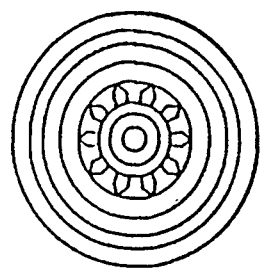

FIGS. 10a and 10b illustrate the bladder application device which is used to insert the bladder electrode constructed in accordance with any one of the embodiments discussed above. FIG. 10b is a side view of the application device illustrating a sheath applicator with a main tube and a shrink wrap covering the wiring leads. A fiber bundle is located in the center of the applicator which would be connected through the lumen illustrated in FIG. 1, for example. The applicator device 175 has an inflation inlet 176 and an electrode wiring insertion port 177 as well as the optical viewing fiber inlet 178 through a lumen. Movement of the bladder electrode 180 is controlled by the alignment guide and the sheath retraction knob 181 acting in conjunction with a thumb detent 182. The applicator of FIG. 10a shows the bladder electrode in an extended but unexpanded position.

Figure 11A:
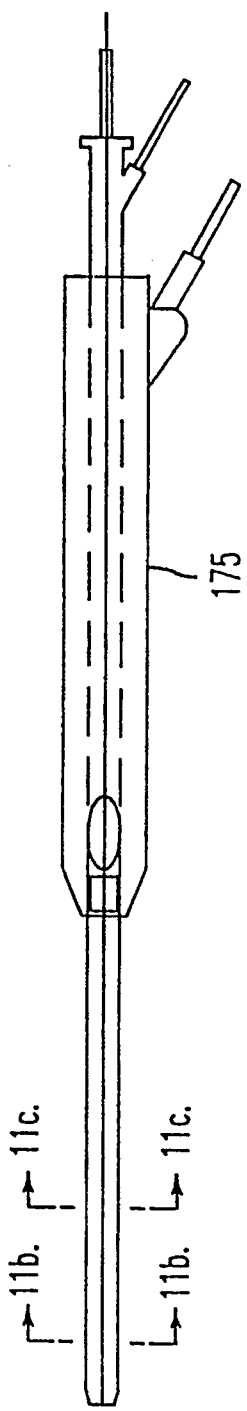
FIGS. 11a-c show the bladder device of FIG. 10 in a retracted position and illustration of the deflated expandable member.
Figure 11C:
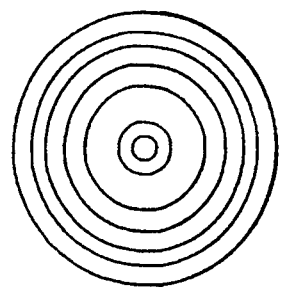
Figure 11B:
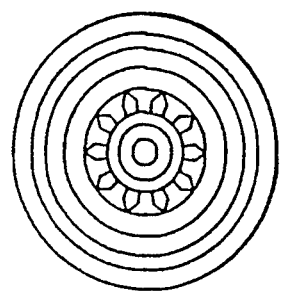

The FIGS. 11a–c illustrate the bladder device of FIG. 10 in a retracted position with FIGS. 11b and 11c being taken at the cross sections titled A—A' and B—B' respectively. FIG. 11c illustrates the position of the deflated bladder with respect to the main tube in the retracted position at line B—B'. The remaining features of the applicator 175 remain as indicated with respect to FIG. 10.

Figure 12:
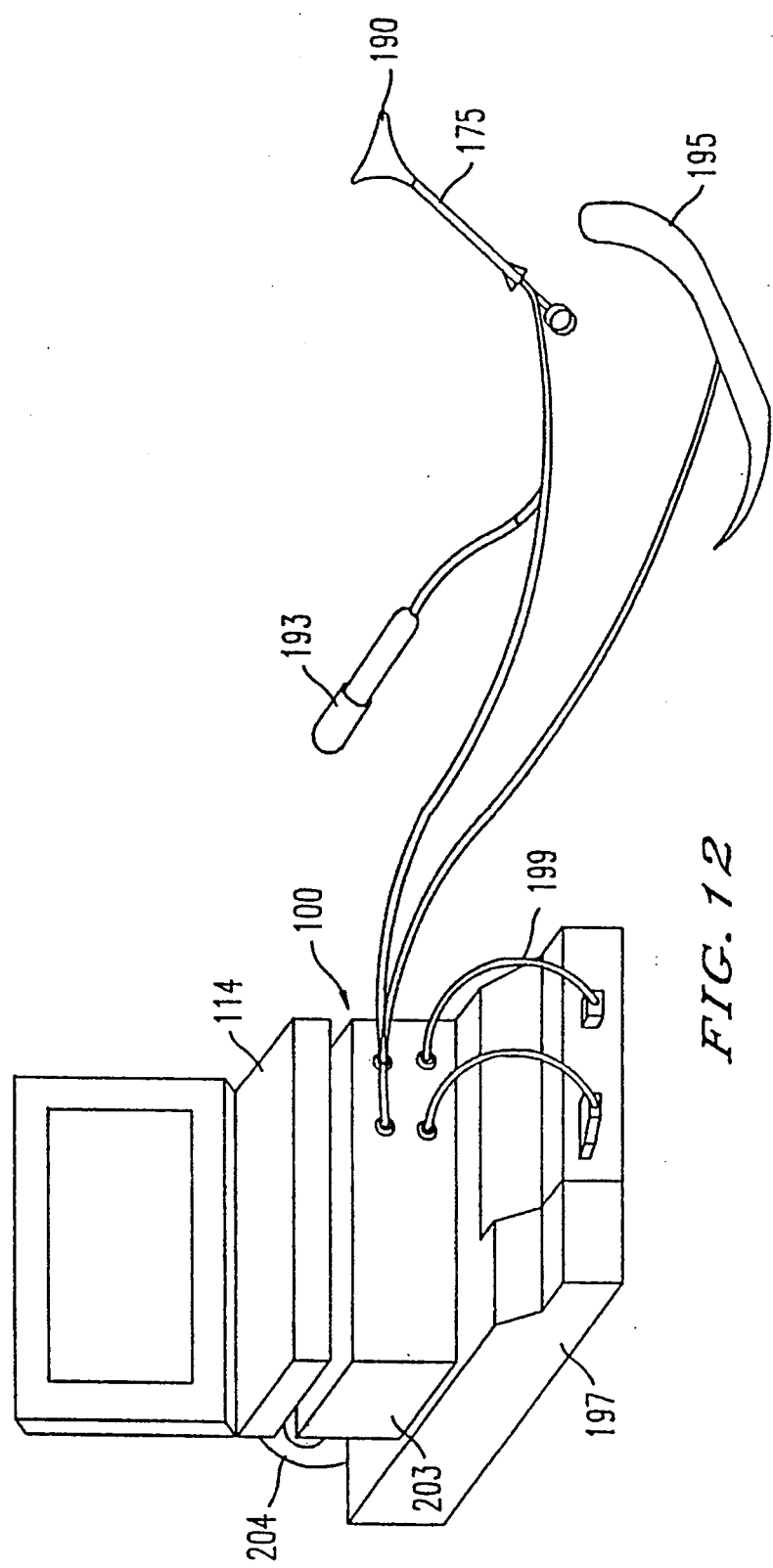
FIG. 12 schematically represents the connection of the bladder device to the power generation source and testing structure.

An illustration of the connection of the application device 175 and the electrode balloon 190 in accordance with any one of the embodiments of the FIGS. 6–9 is illustrated in FIG. 12. An inflation pump 193 provides the medium for the expansion of the balloon 190 while the electrode belt 195 provides the reference electrode for connection to the control system 100. RF generator 197 serves as the RF input power for the control system schematic of FIG. 5 by means of electrosurgical interface cables 199. The control module 203 and interface control 204 connect with computer 114.

Once the electrode system and the control system of FIG. 12 and FIG. 5 are connected, the RF electrodes are separately, independently and sequentially energized with thermistor temperature feedback to bring the endometrial temperature up to a desired level. The system accomplishes this in an automated manner based upon the output from the RF generator 197 which is a conventional electrosurgical power supply. As discussed previously, the electrodes may have a variety of specific configurations and heating is concentrated in the endometrium at the surfaces of the electrodes due to the various illustrated electrode configurations in order to provide uniform heating. An example of the concentration of the heat over the entire surface of the electrode is available from the embodiment wherein holes are provided through the electrode as shown in FIGS. 6 and 8. Uniform heating is also obtained by extending the electrodes in a pattern of lines such as the serpentine pattern structure of FIG. 9.

As a result of these kinds of constructions, the treatment method of the present invention as well as the electrode elements provide an increased current density as a function of the "electrode edge length" available for heating. Furthermore, as discussed previously, the electrodes can be on the outer surface of the bladder while the power traces, thermistors, and thermistor leads can be on the other surface of the bladder.

In the embodiments of FIGS. 6–9, the various electrode pattern feature common power traces for both the electrodes and the associated thermistors. That is, one power lead provides the power for an individual electrode as well as its associated thermistor thereby saving in the construction of the bladder electrodes by reducing the number of required thermistor leads by one-half. In such embodiments, each electrode has a corresponding thermistor lead in common with the RF power lead. The second leads from all thermistors are then connected together to form a thermistor common as shown for example in the FIGS. 7 and 8a. This arrangement provides the advantage that it only requires N+1 leads to drive an ablation balloon with N electrodes and N thermistors. Because of this construction, however, the temperature measurement circuitry 128 of FIG. 5 has additional requirements beyond the construction with a separate power lead for each thermistor and for each individual electrode. The construction with separate power leads for the electrodes and the thermistor are well known and any one of a variety of temperature measurements schemes for individual electrodes could be utilized.

Figure 13:
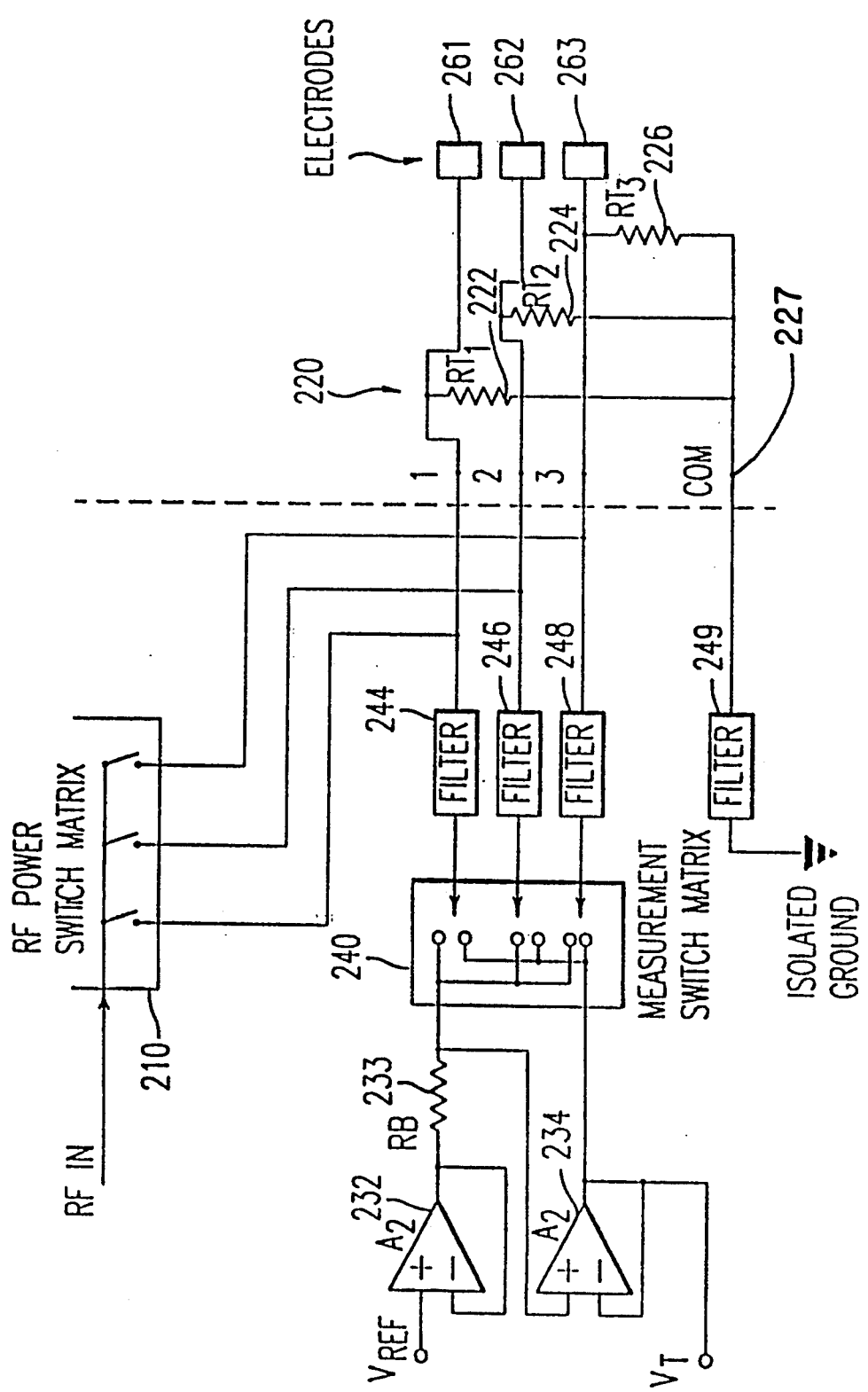
FIG. 13 is a schematic of an embodiment of the temperature measurement circuitry of FIG. 5.

The specialized requirements brought about by using a common power lead for each electrode and each thermistor are met by the embodiment shown in the FIG. 13. In FIG. 13, RF power is selectively applied through switch matrix 210 so that it can be applied to selected electrodes. The electrode/thermistor circuitry is represented on the right hand side of the Figure generally as 220 with a particular example being given by three electrodes and three thermistors represented by resistors 222, 224 and 226. A reference voltage Vref is buffered by an operational amplifier follower 232 and passes through resistor 233 before entering the measurement switch matrix 240. The output of resistor 233 is buffered by operational amplifier 234. Outputs of the measurement switch matrix 240 are fed through the filters 244, 246 and 248 which represent low pass filters which block high frequency RF but pass DC and very low frequency voltages.

The balloon thermistor common lead 227 passes through the filter 249 to ground.

During operation, RF power is applied to a particular desired electrode or electrodes by operations of the RF power switch matrix 210. Measurement of thermistor resistance 222, 224 or 226 is independent of the particular electrodes connected to the RF power. In order to provide a measurement of RT1 (222), measurement switch matrix 240 is set up to connect lead 1 to the right hand side of resistor 233 while all other leads are set to be connected to the output of the follower 234. This particular set up and arrangement forces the voltage VT to be equal to $V_{REF} RT1/(Rb+RT1)$. Therefore this allows the measurement of RT1 due to the known value of Rb and $V_{REF}$. Because the other leads 2, 3 from the circuitry 220 are held at the same voltage by the follower 234, there are no voltage differences between any of these leads and therefore no current will flow between them.

This lack of a current between leads is extremely important because the tissue which contacts the electrodes cause an effective shunt current path that would otherwise affect the measured voltage VT, without the circuitry of FIG. 13.

Figure 14:
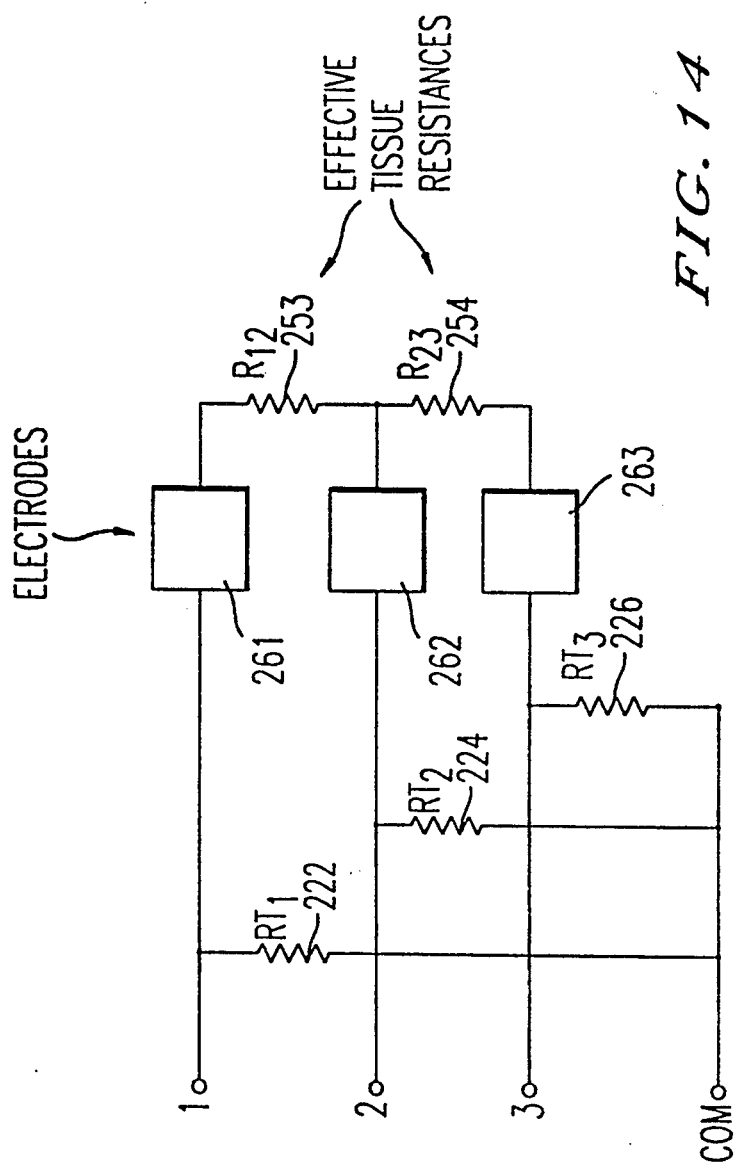
FIG. 14 is an equivalent of FIG. 13 showing effective tissue shunting.

This effective shunting by the tissue is illustrated by the equivalent circuit of FIG. 14 which shows effective tissues resistances 253 and 254 connected between electrodes 261, 262 and 263.

The bladder electrodes are constructed in accordance with a method wherein a double-sided thin flat film is plated on one side to increase the electrode thickness and a deposit mask is provided for an electrode pattern on the thick side using lithographic techniques. Then a mask is deposited for the conductors which lead to the temperature sensing elements on a second side. Subsequently, non-masked conductors are etched away leaving the desired pattern. In an alternate embodiment, the conductive patterns for the electrodes and conductors leading to the temperature sensing elements could be directly deposited using vapor or other deposition techniques.

The thermistors (FIG. 4a) 42 are provided using surface mounting techniques and the attached inner lumen is provided at the center of the flat film. The balloon is then folded and sealed to the main tube at the proximal end with the inner and outer concentric tubes sliding with respect to each other as illustrated in the FIG. 10. Subsequently, conductors are brought to the outside of the main tube to the end of the device near the handle of the applicator. The outer tube is placed over the conductor and heat-shrunk as shown in FIG. 10b. Finally, the handle of the applicator of FIG. 10 or FIG. 11 is assembled.

Other forms of providing an electrode balloon may be used such as utilizing a blow molded preform or the formation of the balloon with copper on polyimide conductive elements on the surface of a compliant balloon. Furthermore, this balloon may be formed as a "sock" to fit over the inner latex balloon with the sock being a compliant device. Other anticipated forms of an electrode balloon structure include the use of the plated or etched wiring all the way from the balloon itself down to the handle.

Utilizing the present invention allows for the use of low accuracy thermistors wherein calibrations can be stored in memory chips in the handles of the device. The attachment of the electrodes to the bladder can be accomplished by conductive adhesive or by soldering.

The applicator of FIGS. 10 and 11 can be deployed by pulling the front end of the balloon back inside and collapsing the balloon around it. In order to expedite the deployment, the pattern can be formed with particular kinds of spines for the sheath in order to aid in the folding of the patterned electrode within the applicator.

Obviously, numerous modifications and variations of the present invention are possible in light of the above teachings. It is therefore to be understood that, within the scope of the appended claims, the invention may be practiced otherwise than as specifically described herein.

What is claimed and desired to be secured by Letters Patent of the United States is:

1. An endometrial ablation apparatus for selectively destroying the endometrial lining of a body organ, said apparatus comprising:
   an electroconductive, expandable electrode means for effecting electrical contact with said endometrial lining to be destroyed, said expandable electrode means containing an electrically non-conductive expansion medium for extending said electrode means to provide said effected electrical contact with said organ;
   a radio frequency power means connected to said expandable electrode means at a frequency greater than 250 kHz for selectively providing current to said electrode means to heat said endometrial lining to a uniform temperature of between 45° C. to 90° C.

2. An endometrial ablation apparatus according to claim 1 wherein said frequency is in a range between 250 kHz and 100 MHz.

3. An endometrial ablation apparatus according to claim 1 wherein said expandable electrode means include an electroconductive balloon and an expansion fluid inlet which is connected to the electroconductive balloon and wherein said balloon is filled with said electrically non-conductive expansion medium.

4. An endometrial ablation apparatus according to claim 3 wherein said balloon is an electroconductive elastomer.

5. An endometrial ablation apparatus according to claim 1 wherein said expandable electrode means is a non-extensible bladder coated with electroconductive material.

6. An endometrial ablation apparatus according to claim 5 wherein an inner surface of said non-extensible bladder is coated with electroconductive material and the bladder wall thickness is less than 0.25 mm.

7. The apparatus according to claim 1 wherein said expandable electrode means includes at least one temperature sensing means.

8. The apparatus according to claim 1 wherein the radio frequency power means includes an output and the apparatus further includes a control means for controlling the output of said radio frequency power means to said expandable electrode means.

9. The apparatus according to claim 8 wherein said control means includes at least one thermistor, having an output, for measuring a temperature of said expandable electrode means and wherein said control means includes means for comparing the output of said at least one thermistor with a reference value and wherein said control means provides an output in response to said means for comparing in order to control the output of said radio frequency power means.

10. The apparatus according to claim 1 wherein said expandable electrode means includes an expandable member and a flat metallized electrode, said expandable member having an outside, said flat metallized electrode being attached to said outside, and wherein said metallized electrode is arranged in a serpentine manner to form a patterned electrode.

11. The apparatus according to claim 1 wherein said radio frequency power means provides current to said electrode means to heat said endometrial lining to a uniform temperature of between 45° C. to 90° C. for a period of ten minutes or less.

12. The apparatus according to claim 1 wherein said expandable electrode means is provided with a plurality of separate electrodes and a thermistor associated with each of said plurality of separate electrodes and further including a plurality of electrode power leads each one of said leads being electrically connected to a respective one of said plurality of separate electrodes and a respective one of said thermistors.

13. The apparatus according to claim 12 further including a temperature measurement circuitry including a first switch matrix means for selectively applying RF power to at least one of said plurality of electrode power leads, a first reference voltage point, a second reference voltage point and a second switch matrix means for connecting a selected one of said plurality of electrode power leads to said first reference voltage point while simultaneously connecting all other ones of said electrode leads to said second reference voltage point.

14. An endometrial ablation apparatus for selectively destroying the endometrial lining of a body organ, said apparatus comprising:
  an electroconductive, expandable electrode means for effecting electrical contact with said endometrial lining to be destroyed, said expandable electrode means containing an electrically non-conductive expansion medium for extending said electrode means to provide said effected electrical contact with said organ, said expandable electrode means being a non-extensible bladder provided with a plurality of separate electrodes; and
  a radio frequency power means connected to said expandable electrode means at a frequency greater than 250 kHz for selectively providing current to said electrode means to heat said endometrial lining to a uniform temperature of between 45° C. to 90° C., said radio frequency power means having an output.

15. The apparatus according to claim 14 wherein each of said electrodes includes a thermistor.

16. The apparatus according to claim 15 further including a control means responsive to an output of each of said thermistors for controlling the output of the said radio frequency power means to said expandable electrode means.

17. An electrically conductive expandable electrode assembly for providing electrical contact with an endometrial lining of a uterus for the purpose of destroying said endometrial lining, said assembly comprising:
  an expandable bladder having an inner surface and an outer surface, one of said inner and said outer surface being provided with a plurality of separate electrodes and the other of said inner and outer surface being provided with a plurality of thermistors corresponding to each of said plurality of electrodes;
  each of said plurality of electrodes further comprising a plurality of holes with one of said plurality of holes of each electrode extending through said bladder from said outside surface to said inside surface and said extended holes providing electrical continuity between said electrodes and said other surface;
  said other surface further including a plurality of power leads, each lead being electrically connected to a corresponding one of said electrodes, said leads each extending from one extremity of said bladder to a respective one of said extended holes, each said power lead also extending to a respective one of said thermistors,
  whereby the relationship between the plurality of holes in each of said electrodes and said power leads provides for uniform heating on a surface of each of the respective electrodes.

18. The expandable electrode assembly according to claim 17 wherein each of said thermistors is further connected to a common ground lead on said other surface.

19. An ablation method for selectively destroying the lining of a body organ having a supporting mass under the lining, said method comprising the steps of:
  passing a radio frequency current having a frequency of at least 250 kHz from an expandable member conforming to the lining and filled with an electrically non-conductive medium, wherein said current is passed through a portion of the lining to resistively heat in a single operation the lining to a temperature within a range from 45° C. to 90° C. for a time sufficient to destroy the cells of the lining while maintaining an average temperature of the supporting mass at a temperature below approximately 42° C.;
  monitoring the temperature of the lining and reducing said current when said monitored temperature exceeds a predetermined value.

20. The method of claim 19 wherein the body organ is a uterus, the lining is the endometrium of the uterus, and the supporting mass is a myometrium of the uterus.

21. The method of claim 19 wherein said portion of the lining includes the entire inner surface of the lining.

22. An ablation method of claim 19 wherein the method comprises an endometrial ablation method for selectively destroying the endometrial lining of a uterus having a myometrium layer under the endometrial lining, said endometrial ablation method comprising the steps of:
  passing a radio frequency current having a frequency of at least 250 kHz from an expandable member conforming to an inner surface of the lining and filled with an electrically non-conductive medium, wherein said current is passed through substantially the entire inner surface of the lining to resistively heat in a single operation said lining to a temperature within a range from 45° C. to 90° C. for a time sufficient to destroy the cells of the lining while maintaining an average temperature of the myometrium at a temperature below approximately 42° C.;
  monitoring the temperature of the surface of said lining and reducing said current when said monitored temperature exceeds a predetermined value.

* * * * *